United States Patent
Westfechtel et al.

(10) Patent No.: US 7,241,910 B2
(45) Date of Patent: Jul. 10, 2007

(54) PROCESSES FOR PRODUCING CONJUGATED LINOLEIC ACID

(75) Inventors: Alfred Westfechtel, Hilden (DE); Wolfgang Albiez, Neuss (DE); Stefan Busch, Oberhausen (DE); Lars Zander, Rommerskirchen (DE); Peter Horlacher, Bellenberg (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 10/523,728

(22) PCT Filed: Jul. 29, 2003

(86) PCT No.: PCT/EP03/08339

§ 371 (c)(1),
(2), (4) Date: Feb. 4, 2005

(87) PCT Pub. No.: WO2004/015046

PCT Pub. Date: Feb. 19, 2004

(65) Prior Publication Data

US 2006/0106238 A1    May 18, 2006

(30) Foreign Application Priority Data

Aug. 7, 2002 (DE) ............................... 102 36 086

(51) Int. Cl.
 *C11C 3/00* (2006.01)
(52) U.S. Cl. ..................................................... 554/126
(58) Field of Classification Search ................. 554/126
 See application file for complete search history.

(56) References Cited

U.S. PATENT DOCUMENTS

| 6,410,761 B1 | 6/2002 | Saebo et al. | |
| 6,414,171 B1 * | 7/2002 | Reaney | 554/126 |
| 2001/0025113 A1 * | 9/2001 | Saebo et al. | 554/223 |

FOREIGN PATENT DOCUMENTS

| DE | 101 43 534 A1 | 3/2003 |
| WO | WO 00/09163 A1 | 2/2000 |

* cited by examiner

*Primary Examiner*—Deborah D. Carr
(74) *Attorney, Agent, or Firm*—John F. Daniels

(57) ABSTRACT

Processes for producing conjugated linoleic acid are described which comprise: (a) isomerizing a linoleic acid lower alkyl ester in the presence of an alkali metal alcoholate to form a conjugated linoleic acid lower alkyl ester; (b) saponifying the conjugated linoleic acid lower alkyl ester in the presence of an aqueous lye to form a saponification product; and (c) neutralizing the saponification product with phosphoric acid.

9 Claims, No Drawings

PROCESSES FOR PRODUCING CONJUGATED LINOLEIC ACID

BACKGROUND OF THE INVENTION

Polyunsaturated linoleic acids with conjugated double bonds, which are commercially available as "CLA" (conjugated linoleic acids), belong to the essential fatty acids for human beings and animals and are therefore used as food additives. Conjugated linoleic acid is normally produced from triglycerides which have a high percentage content of—normally unconjugated—linoleic acid, such as thistle or sunflower oil for example. The triglycerides are isomerized in the presence of basic catalysts and then saponified. A disadvantage in this regard is that, on the one hand, the saponification step yields many unwanted waste materials and, on the other hand, large quantities of alkalis are required, which can quickly result in corrosion in the reactors used. To avoid this, linoleic acid alkyl esters have more recently been used as preferred starting materials and, in a first step, are isomerized to the CLA esters and then saponified. In this process, however, utilization of reactor capacity is often very poor. The profitability of the process is seriously restricted by large volumes of water, poor yields and unwanted secondary products.

Accordingly, the problem addressed by the present invention was to provide a process for the production of conjugated linoleic acid which would be distinguished by very high profitability and which would lead to an end product in high yields and purity.

BRIEF SUMMARY OF THE INVENTION

The present invention relates, in general, to fatty acids and, more particularly, to new processes for the production of conjugated linoleic acid by saponification of its esters and neutralization with phosphoric acid.

The present invention relates to a process for the production of conjugated linoleic acid, in which (a) linoleic acid lower alkyl esters are isomerized in the presence of alkali metal alcoholates, (b) the now conjugated linoleic acid lower alkyl esters are saponified with water in the presence of lye and (c) the saponification product is neutralized with phosphoric acid.

It has surprisingly been found that the neutralization of a saponification product of conjugated linoleic acid lower alkyl esters with phosphoric acid leads to very good utilization of reactor capacity in the production of conjugated fatty acids. Reverse esterification after the saponification step is minimized, so that few unwanted secondary products are formed during the production process. After neutralization with phosphoric acid and subsequent phase separation, an end product is obtained in high yields and high purity by virtue of the low ester content.

DETAILED DESCRIPTION OF THE INVENTION

Conjugated Linoleic Acid Lower Alkyl Esters

Starting materials for the process according to the invention are linoleic acid lower alkyl esters which preferably correspond to formula (I):

$$R^1CO\text{—}OR^2 \qquad (I)$$

where $R^1CO$ is the acyl group of a linoleic acid and $R^2$ is a linear or branched alkyl group containing 1 to 5 carbon atoms. In one particular embodiment, conjugated linoleic acid methyl and/or ethyl esters are used.

Isomerization

The isomerization of the linoleic acid lower alkyl esters is carried out with alkali metal alcoholates in an inert gas atmosphere at temperatures in the range from 90 to 150° C., preferably at temperatures in the range from 100 to 130° C. and more particularly at temperatures in the range from 105 to 125° C.

In a preferred embodiment, alkali metal alcoholates containing 1 to 10 carbon atoms are used as bases during the isomerization, potassium methanolate, potassium ethanolate or potassium-t-butylate being particularly preferred.

Saponification

The saponification of the isomerized linoleic acid lower alkyl esters with aqueous lyes is carried out at temperatures in the range from 40 to 90° C., preferably at temperatures in the range from 60 to 80° C. and more particularly at temperatures in the range from 65 to 75° C. It is continued to a cleavage level of 80 to 100% by weight and preferably above 98%.

Neutralization

The most important step of the process in terms of process economy (high reactor capacity utilization) is the neutralization with phosphoric acid and working up by phase separation, the salts formed remaining dissolved in the aqueous phase. The phosphoric acid is preferably used in a concentration of 75 to 85% by weight for the neutralization step. The neutralization step is also carried out at temperatures of 40 to 90° C., preferably at temperatures of 60 to 80° C. and more particularly at temperatures of 65 to 75° C. Before it is neutralized, the product may be adjusted to the required viscosity by addition of water.

Working Up

The neutralization step is followed by phase separation at a temperature of 50 to 100° C. and preferably at a temperature of 70 to 90° C. The phase separation is optimized by elevated temperatures. It is followed by drying in vacuo at a temperature above 100° C. and preferably at a temperature above 110° C.

EXAMPLE

Production of Conjugated Linoleic Acid from Linoleic Acid Ethyl Ester 1190 g linoleic acid ethyl ester were introduced into a heatable flask and 60 g potassium ethanolate (32% by weight) were then added with stirring under nitrogen at a temperature of 110° C., ethanol being continuously distilled off. After addition of 190 g water, 1070 g of a 25% by weight potassium hydroxide solution were pumped into the flask at a temperature of 70° C. for saponification. Another 770 g water were then introduced with stirring and 510 g phosphoric acid (85% by weight) were added at a temperature of 70° C. for neutralization. Washing water was then removed, followed by phase separation at a temperature of 70 to 90° C.

The conjugated linoleic acid thus obtained had the following characteristics:

| | |
|---|---|
| acid value: | 199 |
| saponification value: | 200 |
| OH value: | 4.9 |
| iodine value: | 162 |
| unsaponifiables: | 0.1% |

What is claimed is:

1. A process for producing conjugated linoleic acid, said process comprising:
   (a) isomerizing a linoleic acid lower alkyl ester in the presence of an alkali metal alcoholate to form a conjugated linoleic acid lower alkyl ester;
   (b) saponifying the conjugated linoleic acid lower alkyl ester in the presence of an aqueous lye to form a saponification product; and
   (c) neutralizing the saponification product with phosphoric acid.

2. The process according to claim 1, wherein the linoleic acid lower alkyl ester corresponds to the general formula (I):

$$R^1CO\text{—}OR^2 \qquad (I)$$

wherein $R^1CO$ represents an acyl linoleyl group and $R^2$ represents a linear or branched alkyl group having from 1 to 5 carbon atoms.

3. The process according to claim 1, wherein the isomerization is carried out at a temperature of from 90 to 150° C.

4. The process according to claim 1, wherein the saponification is carried out at a temperature of from 40 to 90° C.

5. The process according to claim 1, wherein the saponification is carried out until from 80 to 100% by weight of the conjugated linoleic acid lower alkyl ester is saponified.

6. The process according to claim 1, wherein the saponification product is neutralized at a temperature of from 50 to 90° C.

7. The process according to claim 1, further comprising phase separation following neutralization.

8. The process according to claim 7, wherein the phase separation is carried out at a temperature of from 50 to 100° C.

9. A process for producing conjugated linoleic acid, said process comprising:
   (a) isomerizing a linoleic acid lower alkyl ester corresponding to the general formula (I), in the presence of an alkali metal alcoholate to form a conjugated linoleic acid lower alkyl ester, wherein the isomerization is carried out at a temperature of from 90 to 150° C.:

$$R^1CO\text{—}OR^2 \qquad (I)$$

wherein $R^1CO$ represents an acyl linoleyl group and $R^2$ represents a linear or branched alkyl group having from 1 to 5 carbon atoms;
   (b) saponifying the conjugated linoleic acid lower alkyl ester in the presence of an aqueous lye to form a saponification product, wherein the saponification is carried out at a temperature of from 40 to 90° C.; and
   (c) neutralizing the saponification product with phosphoric acid at a temperature of from 50 to 90° C.

* * * * *